(12) United States Patent
Moilliet

(10) Patent No.: US 7,253,303 B2
(45) Date of Patent: Aug. 7, 2007

(54) FLUORINATION OF DICARBONYL COMPOUNDS

(75) Inventor: John Stewart Moilliet, Lancashire (GB)

(73) Assignee: F2 Chemicals Limited (GB)

( * ) Notice: Subject to any disclaimer, the term of this patent is extended or adjusted under 35 U.S.C. 154(b) by 10 days.

(21) Appl. No.: 10/505,083

(22) PCT Filed: Feb. 19, 2003

(86) PCT No.: PCT/GB03/00761

§ 371 (c)(1),
(2), (4) Date: May 10, 2005

(87) PCT Pub. No.: WO03/070677

PCT Pub. Date: Aug. 28, 2003

(65) Prior Publication Data

US 2005/0256332 A1    Nov. 17, 2005

(30) Foreign Application Priority Data

Feb. 20, 2002 (GB) .................... 0203953.5

(51) Int. Cl.
*C07C 69/63* (2006.01)
*C07C 17/00* (2006.01)

(52) U.S. Cl. ..................... 560/227; 570/252

(58) Field of Classification Search ............. 570/123, 570/124, 134, 161, 246, 252, 253; 560/226, 560/227; 568/388, 393
See application file for complete search history.

(56) References Cited

U.S. PATENT DOCUMENTS

2003/0036668 A1* 2/2003 Bowden et al. ............. 570/161

FOREIGN PATENT DOCUMENTS

EP    0 667 332 A1    8/1995
EP    0 781 752 A1    7/1997

OTHER PUBLICATIONS

Inman et al., Reactions of Perchloryl Fluoride with Organic Compounds. II. Fluorination of Certain Active Methylene Compounds, JACS, 80, 6533-5, 1958.*
Accession No. 1550479, Beilstein Database (abstract).
Accession No. 3798709, Beilstein Database (abstract).
Accession No. 1051931, Beilstein Database (abstract).
Accession No. 3385783, Beilstein Database (abstract).
Accession No. 3542074, Beilstein Database (abstract).
Accession No. 3744851, Beilstein Database (abstract).
Accession No. 4819692, Beilstein Database (abstract).
Accession No. 1026198, Beilstein Database (abstract).
GB Search Report Corresponding to Application No. GB 0203953.5, date of search Jul. 30, 2002.
Grakauskas "Direct Liquid-Phase Flourination of Aromatic Compounds" *Journal of Organic Chemistry* 35(3): 723-728 (1970).
International Search Report corresponding to International Application No. PCT/GB03/00761, mailed on Jun. 10, 2003.

* cited by examiner

*Primary Examiner*—Karl Puttlitz
(74) *Attorney, Agent, or Firm*—Myers Bigel Sibley & Sajovec

(57) ABSTRACT

The invention provides a method for the preparation of a dicarbonyl compound of formula (I) $R^1COCFR^2COR^3$ wherein $R^1$ is selected from alkyl, substituted alkyl, cycloalkyl, aryl, substituted aryl and acetoxy, $R^2$ is selected from hydrogen, halogen, nitro, cyano, alkyl, substituted alkyl, cycloalkyl, acetoxy, aryl and substituted aryl, and $R^3$ is selected from alkyl, substitued alkyl, oxyalkyl and substituted oxyalkyl, the method comprising treating a dicarbonyl compound of formula (II) $R^1COCHR^2COR^3$ with elemental fluorine in a solvent which consists of methanol or aqueous methanol. The method provides an inexpensive and convenient synthetic route to 2-fluoro- and 2,2-difluoro-1,3-diketones and -1,3-ketoesters.

15 Claims, No Drawings

FLUORINATION OF DICARBONYL COMPOUNDS

CROSS-REFERENCE TO RELATED APPLICATIONS

The present application is a 35 U.S.C. § 371 National Phase Application of International Application Serial No. PCT/GB03/00761, filed Feb. 19, 2003 and published in English as PCT Publication No. WO 03/070677 on Aug. 28, 2003, which claims priority to Great Britain Patent Application Serial No. 0203953.5, filed Feb. 20, 2002, the disclosures of each of which are incorporated herein by reference in their entireties.

The present invention relates to the preparation of dicarbonyls, in particular dicarbonyl compounds which are 2-fluoro- and 2,2-difluoro-1,3-diketones and -ketoesters.

The use of elemental fluorine for the site specific fluorination of aliphatic compounds is rarely satisfactory due to the high reactivity of the element which leads to unspecific multiple substitution, carbon-carbon bond cleavage and oxidation. Because of the growing importance of fluorinated organic compounds in applications such as in biochemical systems (see, for example Biomedical Aspects of Fluorine Chemistry, R Filler, Y Kobayashi (editors), Elsevier Biomedicinal Press, New York, 1982 and J T Welch, Tetrahedron, 1987, 43, (14), 3123) in recent years considerable effort has gone into finding ways of introducing fluorine into specific sites within molecules to provide building blocks for the preparation of biologically active compounds which have more complex structures. In this context, the replacement of the 2-hydrogen in 1,3-diketones and 1,3-ketoesters is just one transformation that has aroused much interest since the mono- and/or di-fluorinated products can be useful intermediates in the preparation of bio-active molecules. This transformation has been carried out either by treating the 1,3-diketone or 1,3-ketoester, or their metal enolates, with one of several "electrophilic fluorinating agents" that have been developed recently. For example, 1,3-diketones and 1,3-ketoesters have been treated with acetyl hypofluorite (S Rozen and O Lerman, J. Org. Chem., 1983, 48, 724), N-fluoro-pyridinium salts with or without a Lewis Acid catalyst (T Umemoto et al, J. Amer. Chem. Soc., 1990, 112, 8563), xenon difluoride (B Zajc and M Zupan, J. Chem. Soc., Chem. Commun., 1980, 759), lamellar $C_{19}XeF_6$ (H B Kagan, S S Yemul and R Setton, Tetrahedron Letts., 1980, 21, 277), and N-fluorobis[(perfluoroalkyl) sulphonyl]imides (G Resnati and D D Desmarteau, J. Org. Chem., 1992, 57, 4281; Z Xu, D D Desmarteau and Y Gotoh, J. Fluroine Chem., 1992, 58, 71; G Resnatti and D D Desmarteau; J. Org. Chem., 1991 56, 4925; Z Xu, D D Desmarteau and Y Gotoh, J. Chem. Soc., Chem. Commun., 1991, 179) and their metal enolates have been treated with acetyl hypofluorite, as disclosed by Rozen and Lerman, and with N-fluoro-pyridinium salts, according to the method of Umemoto et al.

However, although the treatment of 1,3-diketones and 1,3-ketoesters with electrophilic fluorinating agents can sometimes give high yields of the required mono- or difluorinated products, some of these reagents decompose fairly quickly, and the compounds from which they are made are often expensive or difficult to obtain.

To overcome the various disadvantages associated with the use of electrophilic fluorinating agents, several methods for the direct fluorination of dicarbonyl compounds have been described in the literature. Thus, EP-A-667332 teaches the preparation of fluorine-containing dicarbonyl compounds employing a method which involves treating the dicarbonyl compound with fluorine in at least one solvent selected from halogenated hydrocarbons having 1 to 5 carbon atoms and nitrile compounds. In addition, this document and EP-A-781752 both disclose a fluorination technique wherein a dicarbonyl compound is reacted with fluorine in a solvent in the presence of a salt or an acid having a pKa of 6 or less, and EP-A-748348 specifically describes the fluorination of dicarbonyl compounds in a substantially inert solvent comprising formic acid, the process being carried out substantially in the absence of any acid other than formic acid.

The direct fluorination processes of the prior art do, however, suffer from certain disadvantages. For example, the use of solvents including salts can involve handling two-phase systems, with the attendant problems, whereas acidic solvent systems can lead to difficulties with corrosion of pipework, whilst there are evident toxicity problems involved when dealing with nitrites. In addition, all the direct fluorination methods of the prior art, whilst offering advantages over the earlier techniques involving the use of electrophilic fluorinating agents, still show considerable room for improvement in terms of yield and product quality.

Hence, the present invention seeks to provide a method for the fluorination of dicarbonyl compounds which overcomes the disadvantages of the prior art methods and allows for the preparation of improved yields of products in a higher state of purity.

Thus, according to the present invention, there is provided a method for the preparation of a dicarbonyl compound of formula (I)

$$R^1COCFR^2COR^3 \quad\quad (I)$$

wherein $R^1$ is selected from alkyl, substituted alkyl, cycloalkyl, aryl, substituted aryl and acetoxy, $R^2$ is selected from hydrogen, halogen, nitro, cyano, alkyl, substituted alkyl, cycloalkyl, acetoxy, aryl and substituted aryl, and $R^3$ is selected from alkyl, substituted alkyl, oxyalkyl and substituted oxyalkyl, the method comprising treating a dicarbonyl compound of formula (II)

$$R^1COCHR^2COR^3 \quad\quad (II)$$

with elemental fluorine in a solvent which consists of methanol or aqueous methanol.

Preferably $R^1$ is substituted or unsubstituted alkyl and $R^2$ is hydrogen or substituted or unsubstituted alkyl.

Accordingly, the reaction is carried out substantially in the absence of any other solvent or other additive, and the reaction mixture prior to treatment with elemental fluorine essentially comprises the dicarbonyl compound, methanol and, optionally, water.

The reaction solvent is either 100% methanol, or methanol containing up to 50% water. Preferably, the water content is 20% or less, and particularly favourable results are achieved with water levels of up to 15%.

The reaction may be carried out in a vessel in which the solution is present or alternatively a flowing stream of the solution may be contacted with a gaseous flow of fluorine in countercurrent fashion.

The reaction of the process may be carried out at a temperature in the range from −60° C. to +150° C., although a temperature of from −20° C. to +50° C. is preferred.

The fluorine gas is preferably diluted before use by mixing with an inert gas such as nitrogen or helium. The concentration of fluorine in inert gas is preferably from 1 percent to 50 percent by volume, preferably from 2 percent to 25 percent by volume, especially 5 percent to 15 percent by volume.

The ratio of fluorine to the compound of formula (II) may be varied within wide limits although it is preferred that the molar ratio is in the range from 0.5 to 4.0:1, especially 1.1 to 2.5:1 (fluorine:organic compound).

When fluorination is complete the fluorinated product in the process according to the present invention may be isolated by purging the reaction mixture with inert gas to remove any residual fluorine gas and hydrogen fluoride followed by dilution with excess water or aqueous solution and extraction into a suitable solvent followed by distillation.

Thus the present process according to the present invention provides an inexpensive and convenient synthetic route to 2-fluoro- and 2,2-difluoro-1,3-diketones and -1,3-ketoesters.

Embodiments of the present invention will now be described by way of example only with reference to the following Examples.

EXAMPLES

Example 1

A solution of methyl 3-oxopentanoate (13.0 g, 0.1 mole) in methanol (100 ml) was stirred in an FEP (perfluoropolymer) reactor at −5° C. A gaseous mixture of 10% fluorine in nitrogen was passed through it at 100 ml/min for 28 hrs giving a total of 0.7 moles or 7 equivalents of fluorine.

The reaction solution was drowned into 500 ml water and extracted with 3×50 ml of methylene chloride. The combined organic solutions were dried over magnesium sulphate and rotary evaporated to give 13.9 g of crude product. This was distilled to give 9.1 g of methyl 2-fluoro-3-oxopentanoate, 1.1 g of the starting material and left 1.1 g of residues. This represents a yield of 70% based on consumed starting material at 92% conversion with 9% tar.

Example 2

A similar procedure to example 1 was carried out except the solvent was a mixture of methanol (90 ml) and water (10 ml). The crude weight of product was 13.2 g, which was distilled to give 7.9 g methyl 2-fluoro3-oxopentanoate and 2.9 g starting material, leaving 1.3 g of residue. This represents a yield of 71% at 78% conversion and 12% tar.

Comparative Examples

Example 3

A similar procedure was carried out as in example 1 except that the solvent was acetonitrile (100 ml) and 8.5 equivalents of fluorine were added.

The results gave 4.4 g of methyl 2-fluoro 3-oxopentanoate with 5.7 g of starting material and 1.7 g of heavies (analysable tar-like material). This represents a yield of 55% at a conversion of 56% and 23% heavies.

Example 4

A similar procedure was carried out as outlined in example 1 except that the solvent was methyl formate (100 ml) and 2 equivalents of fluorine were added.

The results showed that the product consisted of 4.9 g of methyl 2-fluoro-3-oxopentanoate, 5.7 g of starting material and 0.8 g of heavies. This represents a yield of 61% at 56% conversion and 11% tar.

The invention claimed is:

1. A method for the preparation of a dicarbonyl compound of formula (I)

$$R^1COCFR^2COR^3 \qquad (I)$$

wherein $R^1$ is selected from alkyl, substituted alkyl, cycloalkyl, aryl, substituted aryl and acetoxy, $R^2$ is selected from hydrogen, halogen, nitro, cyano, alkyl, substituted alkyl, cycloalkyl, acetoxy, aryl and substituted aryl, and R3 is selected from alkyl, substituted alkyl, oxyalkyl and substituted oxyalkyl, the method comprising treating a dicarbonyl compound of formula (II)

$$R^1COCHR^2COR^3 \qquad (II)$$

with fluorine gas in a solvent which consists of methanol or aqueous methanol.

2. The method of claim 1, wherein $R^1$ is substituted or unsubstituted alkyl and $R^2$ is hydrogen or substituted or unsubstituted alkyl.

3. The method of claim 1, wherein the solvent consists of methanol.

4. The method of claim 1, wherein the solvent consists of methanol containing up to 50% water.

5. The method of claim 4, wherein the methanol contains up to 15% water.

6. The method of claim 1, wherein a flowing stream of the solution is contacted with a gaseous flow of fluorine in countercurrent fashion.

7. The method of claim 1, wherein the reaction is carried out at a temperature in the range from −60° C. to +150° C.

8. The method of claim 1, wherein the reaction is carried out at a temperature in the range of from −20° C. to +50° C.

9. The method of claim 1, wherein the fluorine gas is diluted before use by mixing with an inert gas.

10. The method of claim 9, wherein the inert gas comprises nitrogen or helium.

11. The method of claim 9, wherein the concentration of fluorine in inert gas is from 1 per cent to 50 per cent by volume.

12. The method of claim 11, wherein the concentration of fluorine in inert gas is from 5 per cent to 15 per cent by volume.

13. The method of claim 1, wherein the ratio of fluorine to the compound of formula (II) is in the range of from 0.5 to 4.0:1 (fluorine:organic compound).

14. The method of claim 13, wherein the ratio of fluorine to the compound of formula (II) is in the range from 1.1 to 2.5:1 (fluorine:organic compound).

15. The method of claim 1, wherein the fluorinated product is isolated by purging the reaction mixture with inert gas to remove any residual fluorine gas and hydrogen fluoride and the reaction mixture is diluted with excess water or aqueous solution, extracted into a solvent and then distilled.

* * * * *